United States Patent
Charrier et al.

(10) Patent No.: US 9,650,662 B2
(45) Date of Patent: May 16, 2017

(54) METHOD OF SAMPLING AND/OR DEPOSITING A SAMPLE OF BIOLOGICAL MATTER AND DEVICE IMPLEMENTING SUCH A METHOD

(75) Inventors: Jean-Philippe Charrier, Tassin la Demi-Lune (FR); Bruno Colin, Marcy l'Etoile (FR); Laurent Drazek, Grenoble (FR); Cécile Paris, Bessenay (FR); Jean-Claude Raymond, Bessenay (FR); Dominique Decaux, Chaponost (FR)

(73) Assignee: bio Meriéux, S.A., Marcy l'Etoile ( * ) Notice: Subject to any disclaimer, the term of this patent is extended or adjusted under 35 U.S.C. 154(b) by 0 days.

(21) Appl. No.: 13/808,501

(22) PCT Filed: Jul. 8, 2011

(86) PCT No.: PCT/FR2011/051631
§ 371 (c)(1),
(2), (4) Date: Jan. 4, 2013

(87) PCT Pub. No.: WO2012/004545
PCT Pub. Date: Jan. 12, 2012

(65) Prior Publication Data
US 2013/0109047 A1    May 2, 2013

(30) Foreign Application Priority Data
Jul. 8, 2010   (FR) ...................... 10 55565

(51) Int. Cl.
*C12M 1/26* (2006.01)
*C12Q 1/24* (2006.01)

(52) U.S. Cl.
CPC .............. *C12Q 1/24* (2013.01); *C12M 33/04* (2013.01)

(58) Field of Classification Search
CPC ............ G01N 1/42; C12Q 1/24; C12M 33/04
(Continued)

(56) References Cited

U.S. PATENT DOCUMENTS 6,171,280 B1 *  1/2001  Imazu et al. .................. 604/118
6,673,595 B2 *  1/2004  Barbera-Guillem ....... 435/286.2
(Continued)

FOREIGN PATENT DOCUMENTS

EP       0152368     8/1985
EP       1291413     3/2003
(Continued)

OTHER PUBLICATIONS

English language machine translation of JP2006073270 (Mar. 16, 2006), pp. 1-14.*
(Continued)

*Primary Examiner* — William H Beisner

(57) ABSTRACT

The aim of the present invention is a method of sampling all or part of a sample (11) of biological matter (7), which is crude, enriched or cultured through contact with a culture medium (8), such as agar, for example in a Petri dish, using a probe (3) equipped with a terminal end (4), said sampling method comprising the steps of cooling the terminal end (4) of the probe (3), sticking all or part of the sample (11) of biological matter (7) to be sampled through contact, or by applying a pressure exerted by the terminal end (4) onto the sample (11) of biological matter (7), and sampling of all or part of the sample (11) of biological matter (7) so as to separate the sample (11) of biological matter (7) from the culture medium (8), a method of depositing into a container (9) or onto an analysis plate (14) all or part of a sample (11) of biological matter (7) stuck onto a frosted terminal end (4) of a probe, said depositing method including a step of separating the terminal end (4) of the probe (3) from all or (Continued)

part of the sample (11) of biological matter (7), as well as a device (2), a kit and an apparatus (1) implementing these methods.

10 Claims, 7 Drawing Sheets

(58) Field of Classification Search
USPC .................. 435/287.3, 309.1; 73/864.71
See application file for complete search history.

(56) References Cited

U.S. PATENT DOCUMENTS

| | | | |
|---|---|---|---|
| 2003/0068814 A1* | 4/2003 | Malinge | 435/309.1 |
| 2004/0267181 A1 | 12/2004 | Tuite | |
| 2005/0181519 A1* | 8/2005 | Karg et al. | 436/180 |
| 2007/0196817 A1* | 8/2007 | Broom | 435/5 |

FOREIGN PATENT DOCUMENTS

| | | |
|---|---|---|
| JP | 2006073270 A * | 3/2006 |
| WO | WO 03029817 A2 * | 4/2003 |
| WO | WO 2005/018461 | 3/2005 |

OTHER PUBLICATIONS

English language machine translation of WO03029817 (Apr. 10, 2003), pp. 1-4.*
English language International Search Report for PCT/FR2011/051631.
English language Written Opinion for PCT/FR2011/051631.

* cited by examiner

METHOD OF SAMPLING AND/OR DEPOSITING A SAMPLE OF BIOLOGICAL MATTER AND DEVICE IMPLEMENTING SUCH A METHOD

CROSS REFERENCE TO RELATED APPLICATIONS

This application is the national stage application under 35 USC 371 of International Application No. PCT/FR2011/051631, filed Jul. 8, 2011, which claims the benefit of French Patent Application No. 1055565, filed Jul. 8, 2010, the disclosures of which are hereby incorporated by reference.

The aim of the present invention is a method of sampling and a method of depositing a sample of biological matter, crude or enriched cultured through contact with a culture medium, as well as a device implementing these methods.

The sampling of a sample of microorganisms (bacteria, moulds, yeasts or the like) cultured on an agar culture medium in a Petri dish, or on any other support, is currently accomplished with the aid of single-use tools such as oeses, sticks, tubes or cones.

However, these consumables do not make it possible to certainly and efficiently sample all types of microorganisms because the latter can have very different forms, sizes, consistencies, structures or appearances.

On the other hand, these consumables do make it possible to optimally deposit the biological matter on analysis supports such as plates, nor to easily re-suspend said biological matter.

Furthermore, it is important to be able to allow sampling of a bacterial colony or of a fraction of this colony without sampling the culture medium situated under the colony: this could vitiate the analysis results.

The quality of the analysis results also depends on the concentration of the deposit of biological matter formed from the sampled sample, and on its homogeneity on the support on which it is deposited.

The present invention aims to remedy all or some of the disadvantages mentioned above.

To this end, the object of the present invention is a method of sampling all or part of a sample of biological matter, crude, enriched or cultured through contact with a culture medium, possibly agar, using a probe equipped with a terminal end, said sampling method comprising the steps of cooling the terminal end of the probe, sticking all or part of the sample of biological matter to be sampled through contact of the terminal end onto the sample of biological matter, or by applying a pressure exerted by the terminal end onto the sample of biological matter, and sampling all or part of the sample of biological matter so as to separate the sample of biological matter from its support, such as a culture medium.

This method makes it possible to sample any type of sample of biological matter cultured in vitro regardless of form and consistency. Furthermore, with this sampling method, there is no possible contamination of the probe because its end, in contact with the sample, can be sterilised after each use, or is never in direct contact with the sample.

Furthermore, with this sampling method, there is not necessarily any need to use a single-use terminal end, which reduces the cost of use whilst allowing faster use cycles (better productivity of the device).

According to one implementation means, the probe is a cryogenic probe comprising means for being cooled.

According to one implementation of the sampling method, prior to the sticking step, a step of wetting the terminal end of the probe in a liquid solution such as distilled water is carried out, in order to form a layer of ice on the terminal end.

This arrangement allows a consumable to be made extemporaneously which allows the sample to be stuck in order to sample it. Furthermore, with this implementation of the sampling method, the sample is never directly in contact with the terminal end of the probe.

According to one implementation of the method, prior to the sticking step, the sample of biological matter to be sampled is covered with a liquid solution, in order to form a layer of ice around the sample during the step of sticking all or part of said sample to the terminal end of the probe.

According to one implementation of the method, the liquid solution is taken from the group comprising water, a saline solution, a buffer, a liquid culture medium or a matrix commonly used for ionising the sample of biological matter with a view to analysing it using a measuring device such as a mass spectrometer. A buffer may for example a carbonate buffer (10 to 100 mmol/L, ideally 25 mmol/L)

This arrangement makes it possible to reduce by one step the sample mass spectrometer analysis method, the matrix having the double function of being used for the sticking step during sampling and for a sample preparation step with a view to its mass spectrometer analysis.

Alternatively, the liquid solution can be a microorganism culture medium.

According to one implementation of the sampling method, the step of wetting the terminal end of the probe or the sample of biological matter to be sampled in a liquid solution is repeated successively at least twice, in order to form overlaying layers of ice, like a stalactite.

This arrangement makes it possible to enlarge the sticking surface of the stalactite created in this way and thus to be able to sample larger samples.

According to one implementation of the sampling method, the terminal end is removable.

This arrangement makes it possible to considerably increase the useful sticking surface of the terminal end.

According to one implementation of the sampling method, the terminal end possesses ferromagnetic properties.

According to one implementation of the sampling method, the step of sampling all or part of the sample of biological matter consists in applying a magnetic field, for example using an electromagnet, adjacent to the ferromagnetic terminal end so as to attract the terminal end and thus recover it.

This arrangement makes it possible to automate the sampling without risking the contamination of the sampled sample.

Another object of the present invention is a method of depositing into a container or onto an analysis plate all or part of a sample of biological matter stuck onto a frosted terminal end of a probe, said depositing method including a step of separating the terminal end of the probe from all or part of the sample of biological matter stuck onto said terminal end.

This arrangement makes it possible to employ all or part of the sample.

According to one implementation of the depositing method, the separation step is carried out without the sample of biological matter stuck on the frosted terminal end coming into contact with the container or the analysis plate.

In this case, the step of separating the terminal end from all or part of the sample of biological matter stuck on said terminal end is carried out by applying a mechanical shock onto the terminal end.

This arrangement makes it possible to immediately collect all of the sampled sample in a frozen state.

According to one implementation of the depositing method, the step of separating the terminal end from all or part of the sample of biological matter stuck on the frosted terminal end is carried out by a heating means or in ambient air.

This arrangement makes it possible to collect the sample in a liquid state and makes it possible to distribute several parts of the sample on several different supports.

According to one implementation of the depositing method, the separation step is achieved by sequential contact of the sample of biological matter with the container or the analysis plate, this contact bringing about the melting of a superficial layer of ice and the depositing of biological matter.

This arrangement makes it possible to obtain control of the quantity of sample deposited and of the choice of depositing support, and the melting of the superficial layer makes it possible to obtain a homogeneous deposit, both in terms of distribution of biological matter and the depth of the deposited layer.

According to one implementation of the depositing method, all or part of the sample of biological matter is distributed on an analysis plate so as to make several distinct deposits of parts of the same sample of biological matter, which is stuck on the terminal end.

This arrangement makes it possible to take several measurements on the deposits from the same sample, each of these deposits being homogeneous, which makes it possible to improve the quality of certain measurement spectra, in particular for mass spectrometry measurements where a low degree of homogeneity in the deposit leads to spectra comprising less intense peaks with a signal which includes a lot of noise.

According to one implementation of the depositing method, the depositing is effected through continuous contact, for example in the form of lines, of all or part of the sample of biological matter stuck on the terminal end with the container or the analysis plate.

This arrangement makes it possible to achieve a biological matter concentration gradient on the deposit support, and then to focus the measures on the gradient zone which makes it possible to obtain the best results, for example for mass spectrometry measurements.

Another object of the present invention is a device for sampling and depositing all or part of a sample of biological matter, crude, enriched or cultured through contact with a culture medium and intended to be deposited into a container or an analysis plate, characterised in that it comprises: a probe equipped with a terminal end, a cooling means intended for frosting the terminal end, driving means intended to exert a pressure from the probe onto the sample so as to freeze all or part of the water contained in the sample in order to stick it to the terminal end, to separate all or part of the sample from its support, such as a culture medium, to bring all or part of the sample to the container or the analysis plate.

This arrangement provides an automated and reusable device which makes it possible to carry out several sampling and deposition in a minimum amount of time.

According to one embodiment, the device comprises a heating means intended for detaching the sample from the terminal end.

According to a particular embodiment, the heating means is intended for sterilising the terminal end. Such a sterilisation is carrying out before any sampling.

Advantageously, the cooling means and the heating means are composed of at least one Peltier element. Advantageously, several overlaid Peltier elements are used.

This arrangement allows the sample to pass quicker to liquid state and facilitates its re-suspension and homogenisation.

According to one embodiment, the terminal end is metallic or mineral.

This arrangement makes it possible to absorb more quickly the heat contained in the water of the sample, and thus freeze it more quickly.

Advantageously, the terminal end is at least partially covered with a hydrophobic coating or treatment. Such a coating enables easier and optimised drainage of the liquid and/or the sample present on the terminal end when it is unfrozen.

According to one embodiment, the terminal end is removable.

This arrangement makes it possible to separate the frosted terminal end, in order to stick it directly to the sample of biological matter to be sampled.

It furthermore makes it possible to store the terminal end in a refrigerated environment, which can be particularly advantageous if it is desired to carry out an extemporaneous analysis.

According to one embodiment, the terminal end has a shape which optimises the sticking of all or part of the sample of biological matter to be sampled or of liquid solution. According to a particular embodiment, the terminal end comprises a pointed end. Advantageously, the shape of the terminal end can be tapered. Such a shape greatly facilitates the sticking of the sample or of the liquid solution during wetting.

This arrangement makes it possible to precisely sample the sample, but also to sample very small samples such as bacterial microcolonies.

According to one embodiment, the device comprises at least one sensor which controls the pressure exerted by the driving means via the probe in contact with the sample of biological matter to be sampled which is cultured on the culture medium, and does this in order to halt this pressure.

This arrangement makes it possible to prevent any sticking of the sample support, such as an agar culture medium.

According to one embodiment, the sensor is a pressure or force sensor, which can be placed under a Petri dish support for example.

This arrangement makes it possible to control the quantity of biological matter, in the manner of an electronic scale.

According to one embodiment, the device comprises a sensor which detects the contact between the terminal end and the biological matter in order to avoid any pressure.

According to one embodiment, the sensor is a binary electric sensor.

This arrangement makes it possible to prevent any sticking of the sample support, such as an agar culture medium, at lower cost.

Another object of the present invention is a kit comprising a device as described previously, which includes a plurality of interchangeable terminal ends.

These terminal ends may or may not be single-use. They may be pointed, loop-shaped, or cylindrical, and of different sizes. This arrangement makes it possible to have terminal ends of different shapes and sizes for the same device, in order to adapt to the size of the sample to be sampled.

Another object of the present invention is a biological analysis apparatus which contains a device or a kit such as described previously.

In any case, the invention will be better understood with the aid of the following description, with reference to the attached schematic drawings which show, in a non-limiting manner, a device which implements the steps of a method according to the invention.

Figure 1:
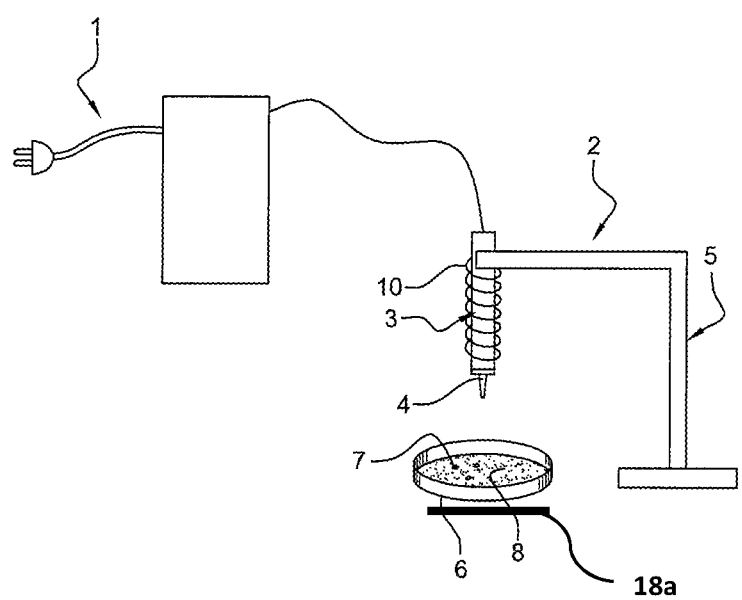
FIG. 1 shows the overview of a device according to the invention.

As depicted in FIG. 1, a sampling and depositing apparatus 1 according to the invention comprises a sampling and depositing device 2.

This sampling and depositing device 2 contains a probe 3, as well as driving means 5 intended for spatial movement of the probe 3.

This driving means 5 may be constituted by automated articulated arms, or any other equivalent means known to the person skilled in the art. Pressure exerted by the driving means 5 is measured by a sensor (18a) which is situated below the Petri dish 6 and which controls the descent of the driving means 5, stopping this descent beyond a specified pressure threshold.

The probe 3 comprises a metal, removable, pointed terminal end 4, which can be replaced by a terminal end 4 with a different-sized point which makes it possible to carry out precise samplings on the biological matter 7.

The probe 3, by the action of the driving means 5, moves above a culture of biological matter 7, constituted here by bacterial colonies cultured on an agar culture medium 8 in a Petri dish 6.

The composition of the biological matter 7 essentially comprises liquid water.

The probe 3 also comprises a cooling means (not shown) for frosting its terminal end 4. This means can for example be constituted by liquid nitrogen routed to the terminal end 4 by a conduit situated in the probe 3 or by depressurising a refrigerant gas in a volume which is in contact with the terminal end 4.

Figure 5:
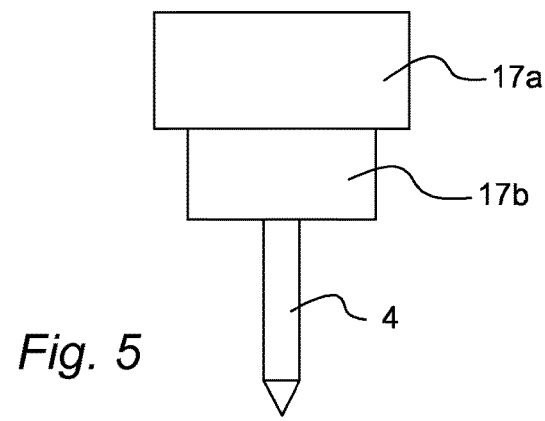
FIG. 5 depicts an embodiment of a cooling means for the terminal end using Peltier elements.

It can also be constituted by one or more Peltier elements in contact with the terminal end 4. In particular, FIG. 5 shows an embodiment in which the cooling means comprise two stages 17a and 17b of Peltier elements on which the terminal end 4 is mounted.

These elements have the advantage of being used for both cooling and heating the terminal end 4, by reversing their electric supply voltage.

In order to prevent heat exchange with the ambient air, it can be advantageous to insulate the upper part of the terminal end 4, which does not come into contact with the sample. This insulation makes it possible to optimise the thermal action of the terminal end 4.

It is in fact possible to envisage having more than two overlaid Peltier elements. The greater the number of elements, the greater the extreme temperatures obtained.

Thus, the cooling and heating of the terminal end 4 will be quicker. It may be possible to envisage using this construction to sterilise the terminal end by heating to a high temperature. This is particularly advantageous in preventing contamination between the different samples of biological matter sampled successively.

The cycle of sampling/depositing biological matter 7 can thus be substantially accelerated and controlled.

The implementation of a sampling method makes it possible to stick to the terminal end 4 of the probe 3 all or part of the sample 11 of the biological matter 7 to be sampled; in this present case, a bacterial colony cultured on the culture medium 8 in a Petri dish 6.

In a first embodiment of the sampling method, a film of ice is deposited on the terminal end 4 by means of the cooling means.

The formation of the film of ice 13 is enabled by the presence of the water contained in the ambient air.

To this end, the device 2 can directly contain a cryogenic source intended for cooling the probe 3 and the terminal end 4.

Figure 2:
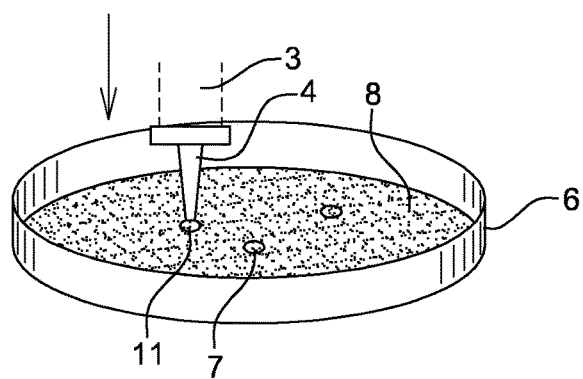
FIG. 2 shows some steps of a sampling method according to a first implementation according to the invention.
Figure 2:
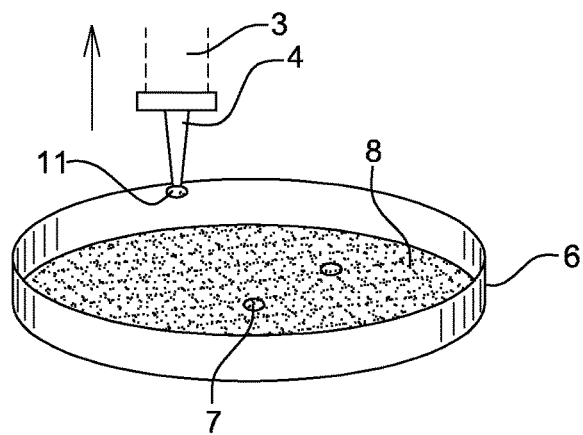
Figure 2:
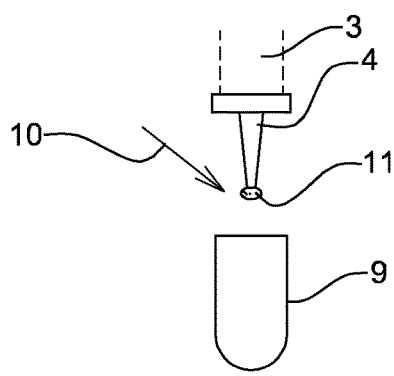
Figure 2:
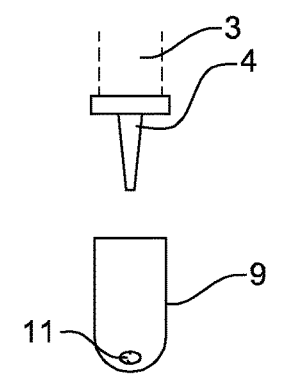

As shown in FIG. 2, the probe 3 with its terminal end 4, via the driving means 5, is brought into contact with the colony 11 of bacteria 7 which has developed on the agar 8 contained in the Petri dish 6.

These driving means 5, via the terminal end 4, apply a pressure on the colony 11 to be sampled. This pressure associated with the low temperature of the film of ice 13 which covers the terminal end 4 makes it possible to freeze the water contained in the bacterial colony 11.

This pressure is measured by a sensor 18a which is situated below the Petri dish 6 and which controls the descent of the driving means 5, stopping this descent beyond a specified pressure threshold.

Alternatively, the terminal end 4 can simply come into contact with the colony 11, without exerting pressure on said colony. To do this, it is useful to have a contact sensor which stops the descent of the driving means 5 once contact is made. Such a sensor may for example be a binary electric sensor.

When it freezes, the water contained in the colony 11 forms a solid block with the layer of ice 13 situated on the surface of the terminal end 4 of the probe 3. All or part of the colony 11 to be sampled is included in the ice, and so is stuck onto the terminal end 4.

The pressure or contact exertion time can be advantageously controlled by the device 2.

Figure 3:
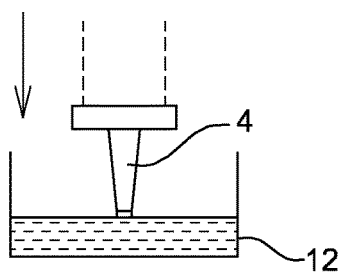
FIG. 3 shows some steps of a sampling method according to a second implementation according to the invention.
Figure 3:
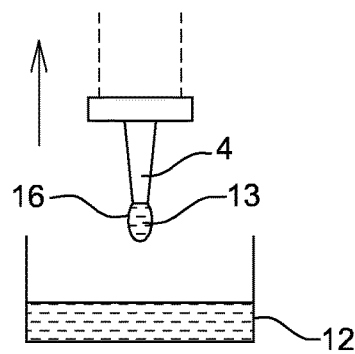
Figure 3:
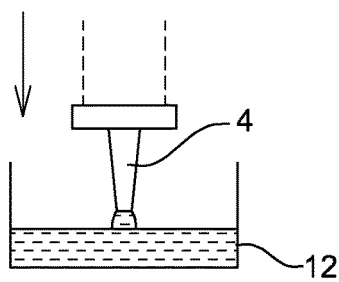
Figure 3:
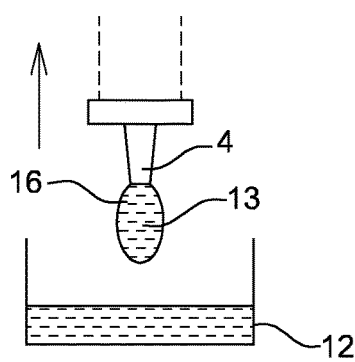

In a second implementation of the sampling method, depicted in FIG. 3, the terminal end 4 of the probe 3 is wetted in a liquid solution 12, such as liquid water or a matrix commonly used for ionising the sample 11 of biological matter 7 with a view to analysing it by a measuring device such as a mass spectrometer.

The liquid solution 12 then forms a layer of ice 13 generally in the form of a drop 16 at the end of the terminal end 4. The drop 16 freezes under the action of the cooling means to form an adhesion surface which comes into contact, via the driving means 5, with the bacterial colony 11 to be sampled.

In a variant of this second implementation of the sampling method also illustrated in FIG. 3, the terminal end 4 of the probe 3 is wetted in the liquid solution 12 several times in succession in order to increase the size of the layer of ice 13 used for the adhesion of the colonies 11 to be sampled.

It is thus possible to adjust the size of this layer of ice 13 to the dimensions of the colony 11 to be sampled.

In these implementations of the sampling method, it can be advantageous to have a terminal end 4 of the probe 3 which has a shape capable of facilitating the attachment of the drop(s) of liquid solution 12 on said end. This shape can be tapered. The end can also have a groove, for example a horizontal groove, on the edge of the end in order to optimise the attachment of the drop of liquid solution 12.

According to a particular embodiment, the container containing the liquid solution can also have a particular shape. Firstly, it is advantageous to have a receptacle with a small volume in line with the volume of the drops(s) to be formed. Secondly, the interior of the container can advantageously have a specified shape correspond to that which the drop must have. Thus, the interior of the receptacle can be tapered. It is moreover beneficial for the container to be deep, insofar as it makes it possible to obtain a relatively long frozen drop and thus limit the risks of contamination of the terminal end 4 by the sample of biological matter.

According to another particular embodiment, the container can have its own cooling means. In that case, the liquid solution 12 contained in the container is cooled. By keeping said liquid solution at a temperature close to its freezing point, it is possible to obtain quicker formation of the frozen drop when the terminal end is dipped into the liquid solution.

In a third implementation of the sampling method (not shown), a drop of liquid solution 12 is deposited onto the colony 11 to be sampled, such that the latter is totally or partially covered in liquid. The terminal end 4 of the probe 3 is then applied onto the drop of liquid solution 12 such that the latter is frozen, trapping all or part of the colony 11 to be sampled and in turn freezing the latter.

In a subsequent step, the driving means 5 separate all or part of the colony 11 from the agar layer 8, thus accomplishing the sampling step.

The driving means 5 make it possible to move the sampled colony 11 above a container 9, such as a test tube 9 or an analysis plate 14, such as an analysis plate used in mass spectrometry.

The implementation of a depositing method subsequently makes it possible to separate the frosted terminal end 4 of the probe 3 from all or part of the colony 11 stuck onto it.

In this first implementation of this depositing method, the separation between the colony 11 and the terminal end 4 is accomplished without contact with any support in ambient air after interruption of the action of the cooling means. Indeed, once the action of the cooling means is interrupted, the ice formed on the terminal end 4 of the probe 3 melts, thus freeing the colony which is stuck to it. It then forms a drop, with a more or less substantial volume depending on the quantity of ice formed initially, in which the bacteria are suspended.

In a variant of this first implementation of the depositing method according to the invention, a heating means 10 contributes to making the ice holding the colony 11 against the terminal end 4 melt more quickly.

This heating means 10 can equally well be constituted by a flame, a hot air welding unit, convergent light rays, the joule effect produced by passing a current into a resistive electrical component, or any other equivalent heat-producing means.

This heating means 10 can also be used subsequently as a sterilising means to sterilise the terminal end 4 of the probe 3.

In the same manner as for the first implementation of the depositing method described above, the colony 11 sampled from the second implementation of the sampling method described above is also separated from the terminal end 4, by means of a heating means 10.

In this implementation of the depositing method, the colony 11 can also be separated from the terminal end 4 of the probe 3 by applying a mechanical shock onto the layer of ice 13.

This mechanical shock causes the layer of ice 13 to break. This is then collected at the same time as the colony 11 sampled in a test tube 9. Such a tube can then be employed for example by an automated analysis system such as the VITEK® 2 automated system, or an analysis plate 14.

According to a second implementation of the depositing method, all or part of the colony 11 is deposited through contact of all or part of the colony 11 onto the analysis plate 14, with this contact progressively melting the superficial layer of ice 13 of the sample by the action on the layer of ice 13 of the surface tension of the surface of the container 9 or of the analysis plate 14.

This contact may be sequential in the form of spots distributed on the analysis plate 14, or continuous in the form of lines.

Depositing in the form of spots makes it possible to obtain a plurality of different deposits from the same sample of sampled biological matter (colony 11). These spots can then be employed for example by a mass spectrometer.

Depositing in the form of continuous lines makes it possible to obtain a concentration gradient of biological matter 7 with stronger concentrations at the start of depositing than at the end of depositing. It is thus possible to take measurements on different zones of the concentration gradient, in order to locate the zone where the analysis results are best, when the mass spectrometer is acquiring measurements.

Figure 4:
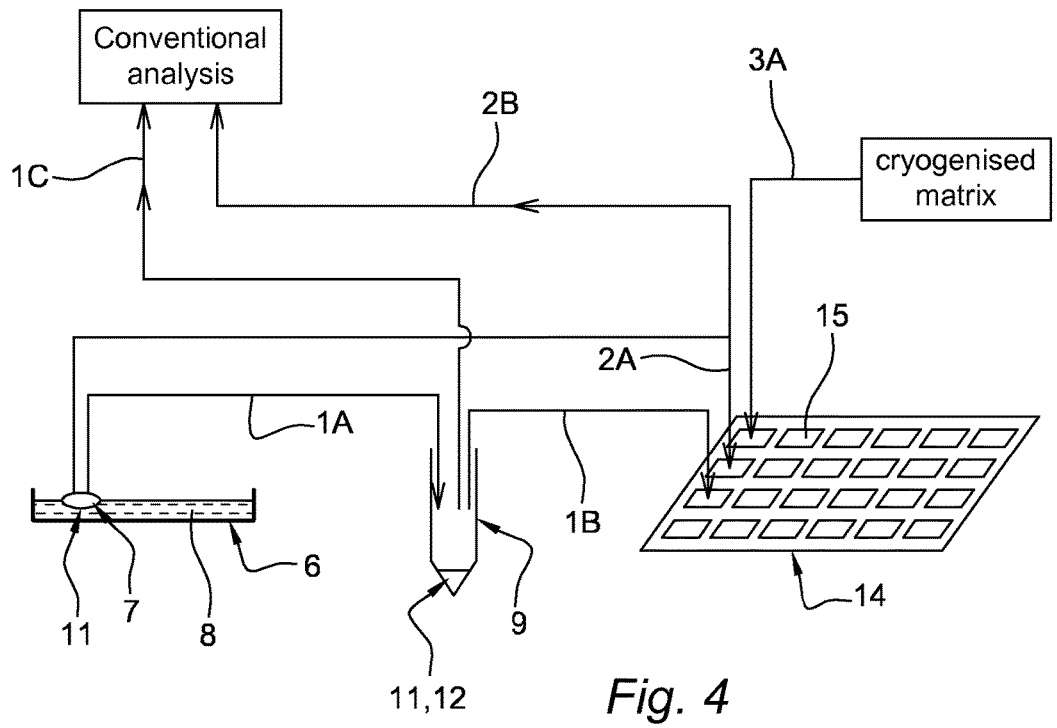
FIG. 4 depicts several examples of sampling and depositing all or part of a sample.

FIG. 4 illustrates some means of implementing the sampling and depositing methods.

In an application 1A corresponding to the sampling method, the entirety or a part of the bacterial colony 11 is directly frozen and then sampled in its Petri dish 6 by the probe 3 to then be deposited in a test tube 9 in which the bacteria will be in suspension after liquefaction of the icicle formed by the probe 3 around its terminal end 4, with a view to undergoing a conventional analysis.

In an application 1B, part of the bacterial suspension contained in the test tube 9 is sampled to be deposited onto the analysis plate 14.

In an application 1C, part of the bacterial suspension contained in the test tube 9 is sampled to be deposited onto another support with a view to a second conventional analysis, for example a test for sensitivity to antibiotics.

In an application 2A, the bacterial colony 11 or a part of this colony is directly frozen and then sampled in the Petri dish 6.

A part of this sampling is deposited directly onto the analysis plate 14 of a mass spectrometer, whilst another part, in an application 2B, is deposited onto another support with a view to a second conventional analysis, for example a test for sensitivity to antibiotics.

The sampling can also be preserved in frozen form on the probe 3 in order to defer the second analysis. This is facilitated if the terminal end 4 is removable. In fact, the terminal end 4 can be preserved in frozen form by depositing this end inside a freezer.

The analysis plate 14 used to accomplish the mass spectrometry analysis of all or part of the colony 11 contains a matrix 15 used to ionise the sample.

In a particular implementation, the matrix 15 is in the form of a dried deposit, after distribution in the form of spots on the analysis plate 14.

The liquefaction of the frozen deposit of all or part of the colony 11 in contact with the analysis plate 14 makes it possible to re-suspend the elements of the matrix 15 in a homogeneous liquid mixture also containing the bacteria.

Another solution, illustrated by the application 3A, consists in sampling the colony 11 in the Petri dish 6 after wetting the terminal end 4 of the probe 3 directly into the matrix 15 which is in its normal form in liquid state, forming an icicle of matrix 15 around the terminal end 4 of the probe 3.

The liquefaction of the frozen deposit in contact with the analysis plate 14, composed of all or part of the colony 11 sampled by the probe 3 and of the matrix 15, will re-suspend the elements of the matrix 15 in a homogeneous liquid mixture also containing the bacteria.

In these two latter embodiments it is important to ensure in advance that the concentration in elements of ionisation matrix will be sufficient with regard to the number of bacteria present in the mixture.

Furthermore, the colonies 11 sampled by these methods, using a non-toxic liquid solution such as water, and reseeded on a Petri dish 6 grow again and are therefore not killed by these sampling and depositing methods.

Examples of industrial applications are suggested below.

EXAMPLES

Example 1

In this first example, an ice tip is used to sample an unknown microorganism colony, and to deposit it on a mass spectrometer target in order to identify the colony of unknown microorganisms using a mass spectrometer in accordance with the following protocol:

sample the colony on blood agar (bioMérieux ref.) with an ice needle, with the ice tip, deposit the colony on a 384-position mass spectrometer target (Bruker). The deposit is obtained by briefly applying the ice tip onto the target at ambient temperature. A slight film of water and microorganisms is thus deposited onto the surface of the target.

deposit 2 µl of matrix (alpha-cyano acid dissolved to 10 mg/ml in a 50/50 solution of acetone and water) at the surface of the sample.

introduce the target into a MALDI-TOF (Ultraflex II, Bruker) mass spectrometer, adjust the mass spectrometer to optimise the acquisition of masses between 2000 and 20000 Da. The person skilled in the art is especially accustomed to adjusting the tension and the laser power of the instrument.

calibrate the mass spectrometer with the benchmark proteins (ProteinMixte, Bruker).

analyse the sample using 20 series of 50 laser shots. The mass spectrum obtained for each series is summed to obtain the mass spectrum of the microorganism. The number of shots can be adjusted by the person skilled in the art to obtain the most informative spectrum possible, i.e. with the most possible and the best defined mass peaks, determine the masses observed on the mass spectrum of the microorganism using the Flex Analysis software (Bruker), compare the masses observed on the mass spectrum of the microorganism with the masses contained in a database. Several databases exist for this purpose: the applicant has its own database, and the databases of the companies Bruker (Biotyper) or Anagnostec (Saramis) can also be used.

identify the microorganism which has the masses closest to those observed on the mass spectrum of the unknown microorganism.

Figure 6:
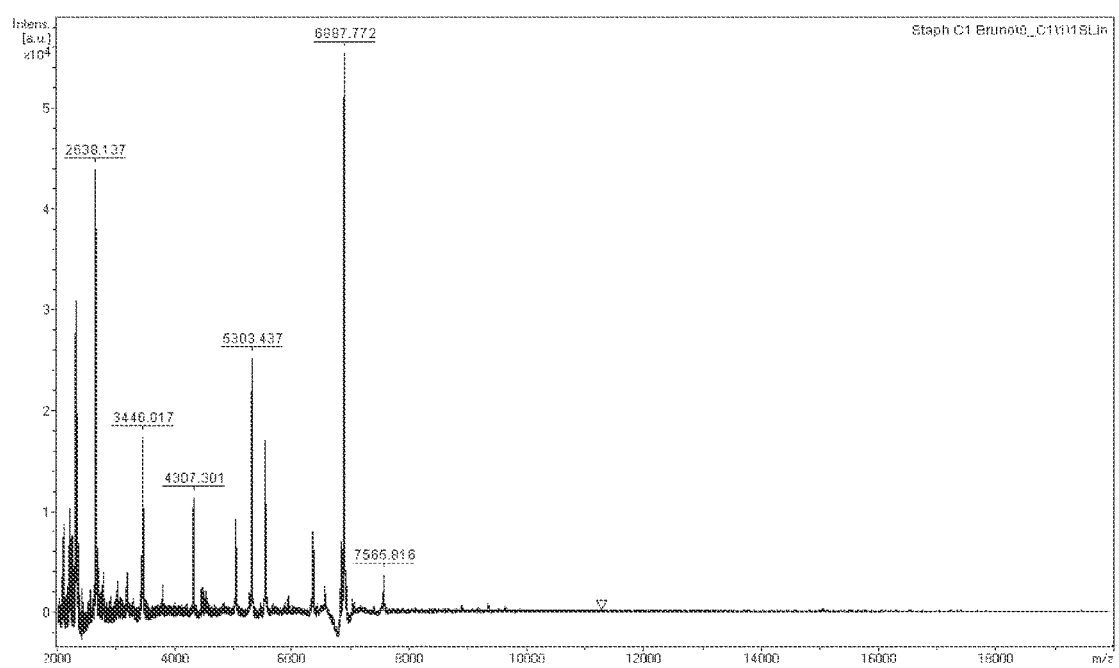
FIG. 6 shows a mass spectrum obtained after sampling and depositing a colony of *Staphylococcus aureus* using the methods according to a first embodiment of the invention.
Figure 7:
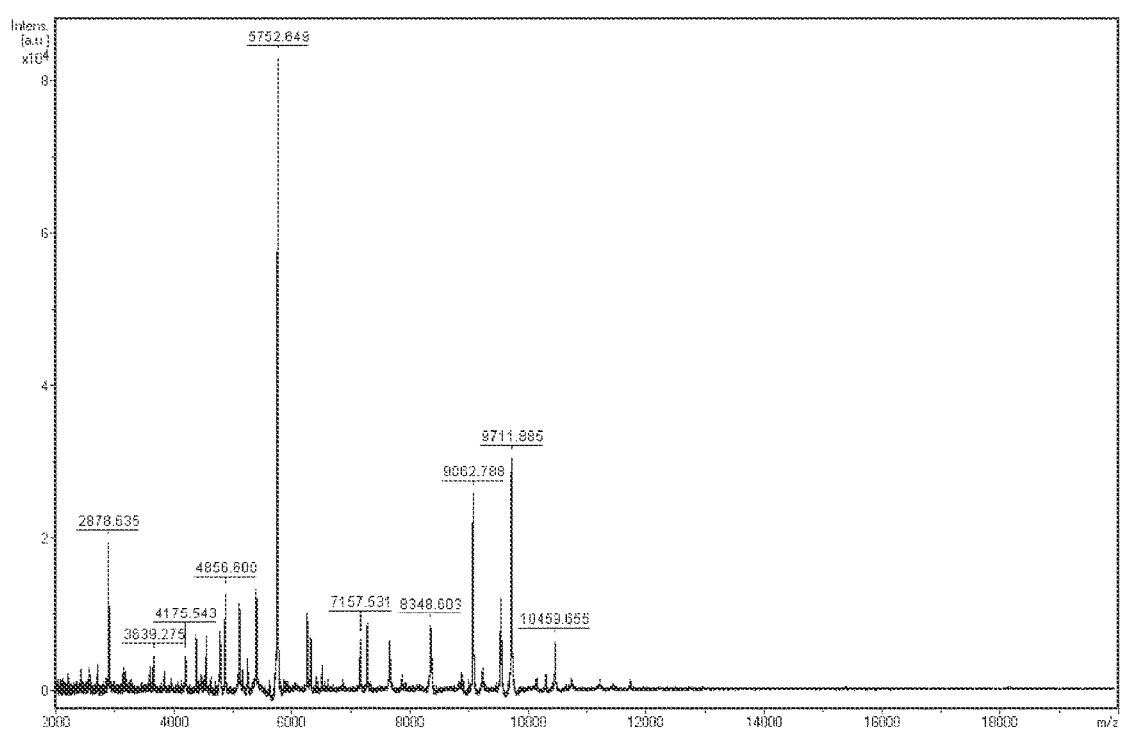
FIG. 7 shows a mass spectrum obtained after sampling and depositing a colony of *Escherichia coli* using the methods according to the first embodiment of the invention.

For this example, this protocol has been applied to two different colonies and has made it possible to obtain the mass spectra visible on FIGS. 6 and 7.

The mass spectrum of FIG. 6 has made it possible to identify the colony as being a *Staphylococcus aureus* colony.

The mass spectrum of FIG. 7 has made it possible to identify the colony as being an *Escherichia coli* colony.

This method is advantageous because it makes it possible to accomplish the sampling and depositing very quickly with an excellent rate of success. From the first attempt, all of the colonies, regardless of their type, are successfully sampled and then deposited by the ice needle.

Furthermore, since the target is at ambient temperature, the ice needle melts very slightly when it touches the surface. The slight stream of water which results from this carries the sample and provides a fine and homogeneous deposit of microorganisms.

This latter point is particularly advantageous because a thick deposit causes signal suppression in mass spectrometry. This phenomenon, which is well known, is due to the excess of salts and a proportion of matrix which is unsuited to the quantity of sample. A heterogeneous deposit is also disadvantageous, as the signal becomes heterogeneous, which makes it difficult to adjust the mass spectrometer.

Example 2

In a second example, the same protocol is implemented as in example 1, with the difference being that in step 2 the deposit is obtained by rubbing the ice tip on the surface of the mass spectrometer target.

Figure 8:
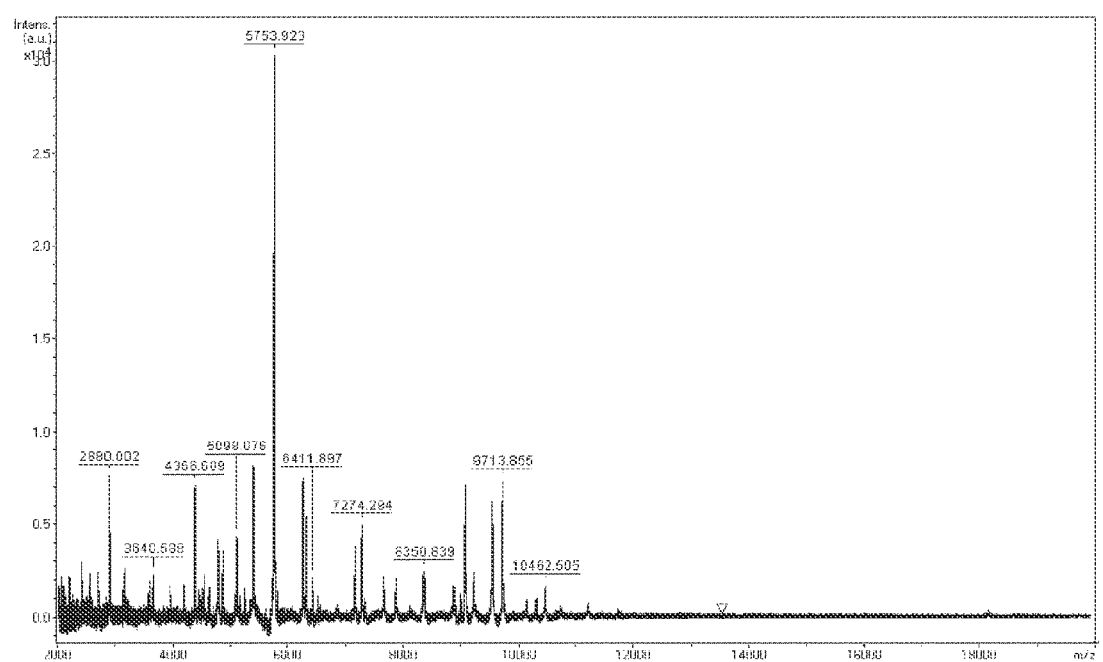
FIG. 8 shows a mass spectrum obtained after sampling and depositing a colony of *Escherichia coli* using the methods according to a second embodiment of the invention.

The spectrum figuring in FIG. 8 is obtained. This spectrum leads to the identification of *Escherichia coli*.

This protocol has the same advantages as example 1. It furthermore makes it possible to deposit over a larger surface, which can be useful for accomplishing several successive acquisitions of the same sample, or for successively acquiring several mass spectra with different parameters.

Example 3

In a third example, 25 strains of known species are cultured in a Petri dish with a COS (Columbia sheep blood medium, bioMérieux, reference 43041) or SDA (Sabouraud glucose medium, bioMérieux, reference 43555) culture medium in accordance with the indications figuring in table 1 below:

TABLE 1

| Culture medium | BioMérieux culture medium reference | Microorganism species | BioMérieux microorganism reference |
|---|---|---|---|
| COS | 43041 | Burkholderia multivorans | 0301039 |
| COS | 43041 | Proteus vulgaris | 0509142 |
| COS | 43041 | Pseudomonas putida | 0509108 |
| COS | 43041 | Streptococcus pseudopneumoniae | 0507105 |
| COS | 43041 | Bacillus licheniformis | 0608016 |
| COS | 43041 | Micrococcus luteus | 0602045 |
| COS | 43041 | Staphylococcus haemolyticus | 0704061 |
| COS | 43041 | Proteus mirabilis | 0805068 |
| COS | 43041 | Enterococcus raffinosus | 0903030 |
| COS | 43041 | Pseudomonas aeruginosa | 1006028 |
| COS | 43041 | Escherichia coli | 1006021 |
| COS | 43041 | Bacteroides fragilis | 1009220 |
| COS | 43041 | Shigella flexneri | 7709005 |
| COS | 43041 | Streptococcus pyogenes | 7701086 |
| COS | 43041 | Streptococcus constellatus ssp constella | 7811150 |
| COS | 43041 | Bacillus megaterium | 8004066 |
| COS | 43041 | Chryseobacterium indologenes | 8105051 |
| COS | 43041 | Vibrio parahaemolyticus | 8305091 |
| COS | 43041 | Citrobacter farmeri | 8608073 |
| COS | 43041 | Aeromonas hydrophila | 606019) |
| COS | 43041 | Salmonella ser. Gallinarum (pullovorum) | 8703202 |
| COS | 43041 | Corynebacterium jeikeium | 9203007 |
| COS | 43041 | Pseudomonas oryzihabitans | 9510157 |
| COS | 43041 | Enterococcus casseliflavus | 9710016 |
| SDA | 43101 | Geotrichum capitatum | 9409060 |

After 16 hours of culturing, for each Petri dish, a colony is sampled with an ice needle and deposited onto a MALDI-TOF target according to the method of the invention. This operation is repeated to obtain two independent deposits for each species studied. The samplings and the deposits are carried out in accordance with the following operating mode.

A metallic tip (terminal end), which is cylindrical with a tapered base, kept at −10° C. by Peltier effect (metallic tip in contact with two Peltier elements in accordance with FIG. 5). It is then dipped for 15 seconds into a receptacle of water kept at 9° C.

The metallic tip is removed from the water. A water drop naturally sticks to the metallic tip. This water drop freezes in 15 seconds by transfer of cold from the metallic tip at −10° C. An ice needle is thus formed.

The needle is positioned on a colony of microorganisms and is immediately withdrawn. The colony of microorganisms instantly adheres to the ice needle and remains stuck on the ice needle. The colony of microorganisms is thus sampled by the ice needle. Conversely, the agar of the culture medium is not picked up.

The colony of microorganisms is deposited onto a disposable 48-position Fleximass DS target from Shimadzu. Each depositing position is a circle with a diameter of 3 mm. Depositing is carried out by rubbing the ice point on the surface of one of the 48 deposit positions of the target with a spiral motion. This motion is initiated at the centre of the depositing position and completed after 4 circuits so as to cover the entire depositing position with a slight film of water and microorganisms.

The sample of microorganisms is dried in open air for several minutes.

1 µL of matrix (alpha-cyano-4-hydroxycinnamic acid ready to be used in solution (bioMérieux, reference 411071) is deposited onto the surface of the sample.

The sample of microorganisms and the matrix are dried in open air for several minutes.

The target is introduced into a MALDI-TOF mass spectrometer (Axima Assurance, Shimadzu) with a FLEXIMASS DS target support (Shimadzu).

The mass spectrometer is adjusted to optimise the acquisition of masses between 2000 and 20000 Da. The person skilled in the art is especially accustomed to adjusting the tension and the laser power of the instrument.

The mass spectrometer is calibrated with a deposit of E. coli (ATCC 8739 strain).

The sample is analysed using 100 series of 5 laser shots. The mass spectrum obtained for each series is summed to obtain the mass spectrum of the microorganism. The number of shots can be adjusted by the person skilled in the art to obtain the most informative spectrum possible, i.e. with the most possible and the best defined mass peaks.

the masses observed on the mass spectrum of the microorganism are determined with the aid of the LaunchPad version 2.8 software (Shimadzu), The masses observed on the mass spectrum of the microorganism are compared with the masses contained in the Saramis (bioMérieux) database using the Spectral ID version 1.1.0 interface (bioMérieux), and the microorganism is identified by comparison with the mass spectra of microorganisms present in the database.

For this example, the protocol has made it possible to identify the deposits according to the results set out in table 2 below:

TABLE 2

| Expected microorganism species | Deposit No. 1 Species identified with the protocol from example 3 | Probability of identification (%) | Deposit No. 2 Species identified with the protocol from example 3 | Probability of identification (%) |
|---|---|---|---|---|
| Burkholderia multivorans | Burkhol. multivorans | 100 | Burkhol. multivorans | 100 |
| Proteus vulgaris | Proteus vulgaris | 100 | Proteus vulgaris | 99.99 |
| Pseudomonas putida | Ps. putida | 99.99 | Ps. putida | 99.99 |
| Streptococcus pseudopneumoniae | no identification | — | Str. pseudopneumoniae | 65.67 |
| Bacillus licheniformis | B. licheniformis | 100 | B. licheniformis | 99.99 |
| Micrococcus luteus | Mic. luteus/lylae | 99.99 | Mic. luteus/lylae | 100 |
| Staphylococcus | Staph. haemolyticus | 99.99 | Staph. haemolyticus | 99.99 |

TABLE 2-continued

| Expected microorganism species | Deposit No. 1 | | Deposit No. 2 | |
|---|---|---|---|---|
| | Species identified with the protocol from example 3 | Probability of identification (%) | Species identified with the protocol from example 3 | Probability of identification (%) |
| haemolyticus | | | | |
| Proteus mirabilis | Proteus mirabilis | 100 | Proteus mirabilis | 100 |
| Enterococcus raffinosus | Entero. raffinosus | 99.99 | Entero. raffinosus | 100 |
| Pseudomonas aeruginosa | Ps. aeruginosa | 99.99 | Ps. aeruginosa | 99.99 |
| Escherichia coli | Esch. coli | 99.99 | Esch. coli | 99.99 |
| Bacteroides fragilis | Bac. fragilis | 99.99 | Bac. fragilis | 99.99 |
| Shigella flexneri | Esch. coli | 99.99 | Esch. coli | 99.99 |
| Streptococcus pyogenes | Str. pyogenes | 100 | Str. pyogenes | 99.99 |
| Streptococcus constellatus ssp constella | Str. constellatus | 99.9 | no identification | — |
| Bacillus megaterium | B. megaterium | 99.99 | B. megaterium | 99.99 |
| Chryseobacterium indologenes | Chryse. indologenes | 99.99 | Chryse. indologenes | 99.99 |
| Vibrio parahaemolyticus | V. parahaemolyticus | 100 | V. parahaemolyticus | 99.99 |
| Citrobacter farmeri | Citro. farmeri | 99.99 | Citro. farmeri | 99.99 |
| Aeromonas hydrophila | Aer. salm. salmonicida or Aer. hydro./caviae | 99.99 or 99.73 | Aer. salm. salmonicida or Aer. hydro./caviae | 99.99 or 98.16 |
| Salmonella ser. Gallinarum (pullovorum) | Salmonella group | 78.25 | Salmonella group | 78.15 |
| Corynebacterium jeikeium | Coryn. jeikeium | 100 | Coryn. jeikeium | 100 |
| Pseudomonas oryzihabitans | Ps. oryzihabitans | 99.99 | Ps. oryzihabitans | 99.99 |
| Enterococcus casseliflavus | Entero. casseliflavus | 100 | No identification | — |
| Geotrichum capitatum | G. capitatum | 100 | G. capitatum | 100 |

The species identified corresponds exactly to the species expected, taking into account the comments below:

Spectral ID provides the abbreviated name of the species. The person skilled in the art is accustomed to these abbreviations. By way of example, it is clear to him that *G. capitatum* means *Geotrichum capitatum*, that *Entero.casseliflavus* means *Enterococcus casseliflavus*, and so on.

*Micrococcus luteus* is identified as *Mic.luteus/lylae*, i.e. as possibly being *Micrococcus luteus* or *Micrococcus lylae*. It is not possible to differentiate between these two species using MALDI-TOF analysis and the Saramis database.

*Shigella flexneri* is identified as *Esch.coli*, i.e. *Escherichia coli*. As above, *Shigella flexneri* and *Escherichia coli* are two species which are too close to be distinguishable by MALDI-TOF. Spectral ID and Saramis class these two species as *Escherichia coli*.

*Aeromonas hydrophila* is identified as *Aer.salm.salmonicida* or *Aer.hydro./caviae*. The 3 species are very close and are difficult to differentiate by MALDI-TOF.

*Salmonella* ser. *Gallinarum* (*pullovorum*) is identified as *Salmonella* group. MALDI-TOF analysis does not have sufficient resolution to unequivocally distinguish serovar *Gallinarum* (*pullovorum*) from the other serovars. The Spectral ID software and Saramis therefore give only one identification at the level of the *Salmonella* genus.

The protocol has thus made it possible to identify all of the analysed species. 72 deposits out of 75 have been identified, which represents 97.3% correct identification. This identification rate is very good, indeed even better than the person skilled in the art is accustomed to obtain with manual sampling and deposition followed by a MALDI-TOF analysis.

This method is advantageous because it makes it possible to accomplish the sampling and depositing very quickly with an excellent rate of success and for any type of microorganism (bacteria or yeast (*G. capitatum*)). In particular, this method makes it possible to sample, and deposit with equal effectiveness, microorganisms which have very different forms and consistencies (*Proteus, Bacillus*, coliforms, etc.).

Although the invention has been described in connection with particular implementation examples and embodiment examples of the invention, it is clear that it is by no means limited by these and that it encompasses all of the equivalent techniques of the steps and means described, and combinations thereof.

The invention claimed is:

1. A device for sampling and depositing (2) all or part of a sample (11) of biological matter (7), which is crude, enriched or cultured through contact with a semi-solid culture medium such as an agar medium (8), and intended to be deposited into a container (9) or onto an analysis plate (14), characterised in that it comprises:
   a probe (3) equipped with a pointed and closed terminal end (4),
   a cooling means intended for frosting the terminal end (4),
   driving means (5) intended: for exerting a pressure from the probe (3) onto the sample (11) so as to freeze all or part of the water contained in the sample (11) in order to stick it to the terminal end (4), for separating all or part of the sample (11) from the culture medium (8), to bring all or part of the sample (11) to the container (9) or the analysis plate (14) and at least one sensor which controls the pressure exerted by the driving means (5) via the probe (3) to stop penetration of the culture medium (8).

2. The device (2) according to claim 1, comprising a heating means (10) intended for detaching the sample (11) from the terminal end (4).

3. The device (2) according to claim 2, wherein the heating means (10) is also intended for sterilising the terminal end (4).

4. The device (2) according to claim 1, wherein the cooling means and the heating means are composed of at least one Peltier element.

5. The device (2) according to claim 1, wherein the terminal end (4) is metallic or mineral.

6. The device (2) according to claim 1, wherein the terminal end (4) is at least partially covered with a hydrophobic coating or treatment.

7. The device (2) according to claim 1, wherein the terminal end (4) is removable.

8. The device (2) according to claim 1, wherein the terminal end has a shape which optimises the sticking of all or part of the sample (11) of biological matter (7) to be sampled or of the liquid solution (12).

9. The device (2) according to claim 1, wherein the sensor is a pressure or force sensor.

10. A kit comprising a device according to claim 1 including a plurality of interchangeable terminal ends (4).

* * * * *